(12) United States Patent
Waugh et al.

(10) Patent No.: US 8,268,000 B2
(45) Date of Patent: Sep. 18, 2012

(54) COMPOSITE INTERBODY SPACER

(75) Inventors: Lindsey G. Waugh, Memphis, TN (US); Matthew D. Schultz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1347 days.

(21) Appl. No.: 11/695,979

(22) Filed: Apr. 3, 2007

(65) Prior Publication Data
US 2008/0249625 A1 Oct. 9, 2008

(51) Int. Cl.
*A61F 2/44* (2006.01)
(52) U.S. Cl. .................................. 623/17.16
(58) Field of Classification Search ..... 623/17.11–17.16
See application file for complete search history.

(56) References Cited

U.S. PATENT DOCUMENTS

| | | | |
|---|---|---|---|
| 4,403,606 A * | 9/1983 | Woo et al. ............. | 606/70 |
| 4,904,261 A | 2/1990 | Dove et al. | |
| 5,397,364 A | 3/1995 | Kozak et al. | |
| 5,534,031 A * | 7/1996 | Matsuzaki et al. ......... | 623/17.11 |
| 5,876,402 A | 3/1999 | Errico et al. | |
| 5,888,223 A | 3/1999 | Bray, Jr. | |
| 5,931,838 A | 8/1999 | Vito | |
| 6,235,059 B1 | 5/2001 | Benezech et al. | |
| 6,261,291 B1 | 7/2001 | Talaber et al. | |
| 6,331,179 B1 | 12/2001 | Freid et al. | |
| 6,468,311 B2 | 10/2002 | Boyd et al. | |
| 6,533,786 B1 | 3/2003 | Needham et al. | |
| 6,562,074 B2 * | 5/2003 | Gerbec et al. ........... | 623/17.15 |
| 6,569,201 B2 * | 5/2003 | Moumene et al. ......... | 623/17.11 |
| 6,579,290 B1 | 6/2003 | Hardcastle et al. | |
| 6,592,586 B1 | 7/2003 | Michelson | |
| 6,602,255 B1 | 8/2003 | Campbell et al. | |
| 6,613,091 B1 | 9/2003 | Zdeblick et al. | |
| 6,629,998 B1 * | 10/2003 | Lin ........................ | 623/17.11 |
| 7,001,389 B1 | 2/2006 | Navarro et al. | |
| 7,025,769 B1 | 4/2006 | Ferree | |
| 7,135,043 B2 * | 11/2006 | Nakahara et al. ......... | 623/17.11 |
| 7,232,464 B2 * | 6/2007 | Mathieu et al. ........... | 623/17.11 |
| 7,556,651 B2 * | 7/2009 | Humphreys et al. ....... | 623/17.15 |
| 7,794,502 B2 * | 9/2010 | Michelson ................ | 623/17.16 |
| 2002/0022843 A1 | 2/2002 | Michelson | |
| 2002/0099376 A1 | 7/2002 | Michelson | |
| 2002/0151899 A1 | 10/2002 | Bailey et al. | |
| 2002/0169508 A1 | 11/2002 | Songer et al. | |
| 2003/0078583 A1 | 4/2003 | Biedermann et al. | |
| 2004/0030338 A1 | 2/2004 | Paul | |
| 2005/0043736 A1 * | 2/2005 | Mathieu et al. ............. | 606/73 |
| 2005/0071006 A1 | 3/2005 | Kirschman | |
| 2005/0192577 A1 | 9/2005 | Mosca et al. | |
| 2006/0085071 A1 | 4/2006 | Lechmann et al. | |
| 2008/0119934 A1 * | 5/2008 | Eckhardt ................. | 623/17.16 |

FOREIGN PATENT DOCUMENTS

WO    WO 00/78238    12/2000

OTHER PUBLICATIONS

"Solution auto-stable pour les fusions intersomatiques par voie anterieure", Synthes, 1 page.

* cited by examiner

*Primary Examiner* — Eduardo C Robert
*Assistant Examiner* — Jerry Cumberledge (57) ABSTRACT

A composite interbody spacer includes a first portion formed of a first material and a second portion formed of a second material.

32 Claims, 8 Drawing Sheets

COMPOSITE INTERBODY SPACER

FIELD OF THE INVENTION

The present invention relates generally to the field of medical implants secured by bone anchors.

BACKGROUND

Spinal discs between the endplates of adjacent vertebrae in a spinal column of the human body provide critical support. However, due to injury, degradation, disease or the like, these discs can rupture, degenerate and/or protrude to such a degree that the intervertebral space between adjacent vertebrae collapses as the disc loses at least a part of its support function. This can cause impingement of the nerve roots and severe pain. In some cases, surgical correction may be required.

Some surgical corrections include the removal of the natural spinal disc from between the adjacent vertebrae. In order to preserve the intervertebral disc space for proper spinal-column function, an interbody spacer can be inserted between the adjacent vertebrae.

Some interbody spacers employ bone anchors that fix the interbody spacer in place between the adjacent vertebrae. Conventional interbody spacers are formed of a biocompatible metal, such as titanium. However, titanium interbody spacers are rigid and provide little cushioning. In extreme situations, this may be a cause of subsidence, which can generate additional pain and trauma to a spinal column.

What is needed is an implantable device that provides a cushioned support. The implantable devices disclosed herein address one or more deficiencies in the art.

SUMMARY

In a first exemplary aspect, the present disclosure is directed to a composite interbody spacer. The spacer may include a first portion being formed of a first material. The first portion may be configured as a load bearing portion and having a first bore formed therein. The second portion may be formed of a second material and may be at least partially disposed within the first bore in a manner that reinforces the first bore and in a manner to interface with a bone anchor extending through the first bore.

In another exemplary embodiment, the second portion may have a second bore formed therein that is at least partially disposed within the first bore in a manner that a bone anchor can extend through the first and second bores.

In another exemplary aspect, an implantable device includes the composite interbody spacer and a bone anchor extending through the first and second bores.

In yet another exemplary aspect, the present disclosure is directed to a composite interbody spacer that may include a first portion formed of a first material and configured for placement between an upper and a lower vertebra as a load bearing portion. The first portion may have a first end surface with a first connecting feature extending therethrough into the first portion. A second portion may be formed of a second material and may have a bore formed therein for receiving an anchor, and may have a second connecting feature extending therefrom. The second connecting feature may be configured to extend through the first end surface and into the first connecting portion.

In another exemplary aspect, the first portion has a U-shape having a first end and a second end. The second portion may extend from the first end to the second end, and the first connecting feature may be formed in one of the first and second ends. In yet another exemplary aspect, the first portion may include exterior sides, with the first connecting feature being formed in the exterior sides.

In another exemplary aspect, the present disclosure is directed to a composite interbody spacer that may include a U-shaped first portion that may be formed of a first material and may have a first and a second end. The first portion may be configured as a load bearing portion for placement between an upper and a lower vertebra. The first portion may include a first connecting feature. A second portion may be formed of a second material and may be disposed to extend from the first end to the second end. The second portion may have a bore formed therein for receiving a bone anchor. A second connecting feature may be configured to cooperate with the first connecting feature to connect the first and second portions.

In some exemplary aspect, the first and second portions together define a hollow region.

In yet another exemplary aspect, the present disclosure is directed to a method including introducing an interbody spacer to a vertebral segment comprising an upper and a lower vertebra. The interbody spacer may have a first portion formed of a first material, may be configured as a load bearing portion, and may have a first bore formed therein. The spacer may have a second portion being formed of a second material, may have a second bore formed therein, and may be at least partially disposed within the first bore in a manner that a bone anchor can extend through the first and second bores. The method also may include inserting a bone anchor into the first and second bores and may include tightening the bone anchor to penetrate a vertebra.

Further aspects, forms, embodiments, objects, features, benefits, and advantages of the present invention shall become apparent from the detailed drawings and descriptions provided herein.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
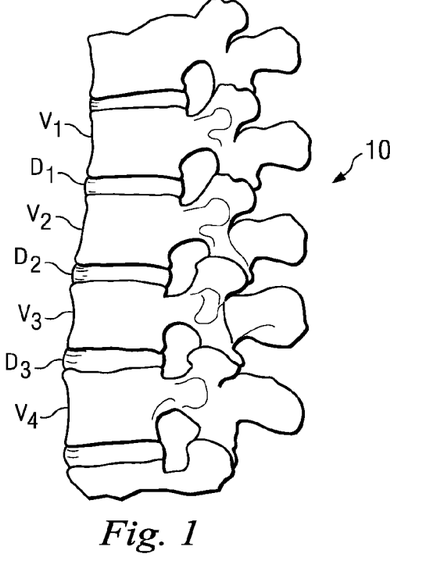
FIG. 1 is an illustration of a lateral view of a segment of a lumbar spine.

FIG. 1 shows a lateral view of a portion of a spinal column 10, illustrating a group of adjacent upper and lower vertebrae V1, V2, V3, V4 separated by natural intervertebral discs D1, D2, D3. The illustration of four vertebrae is only intended as an example. Another example would be a sacrum and one vertebra.

Figure 2:
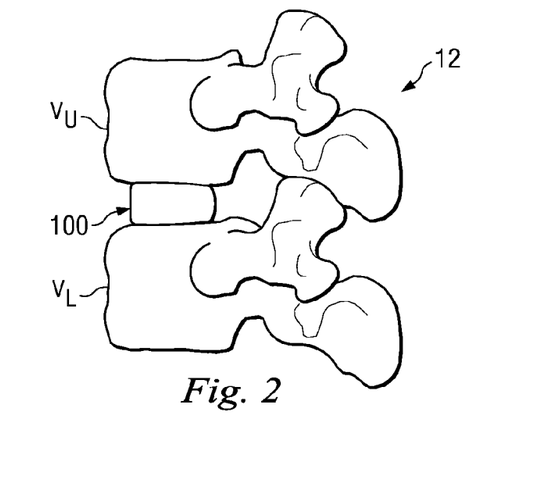
FIG. 2 is an illustration of a lateral view of a spinal segment formed by two vertebrae with an exemplary implantable device disposed therebetween.

For the sake of further example, two of the vertebrae will be discussed with reference to a spinal segment 12 shown in FIG. 2. An upper vertebra 14 and a lower vertebra 16, which may be any of the vertebrae V1, V2, V3, V4, define the spinal segment 12. Although the illustrations of FIGS. 1 and 2 generally depict a lumbar vertebrae and a lumbar vertebral segment, it is understood that the devices, systems, and methods of this disclosure may also be applied to all regions of the vertebral column, including the cervical and thoracic regions.

Some types of disc arthroplasty require that a part of or the entire natural disc that would have been positioned between the two vertebrae 14, 16 be removed via a discectomy or a similar surgical procedure. Removal of the diseased or degenerated disc results in the formation of an intervertebral space between the upper and lower vertebrae 14, 16. Once the diseased or degenerated disc is removed, an implantable prosthetic device may be used to maintain the vertebral spacing and provide vertebral support. As shown in FIG. 2, an implantable device, referenced herein by the reference numeral 100, resides within the vertebral space. Sized to fit the disc space height in a manner similar to a natural intervertebral disc, such as any of discs D1-D4, the implantable device 100 provides support and stabilization to the vertebrae.

The implantable device 100 is configured to interface with the bearing endplates of the vertebrae 14, 16. To maximize compatibility, it may be formed of a material having properties not unlike those of natural bone or the natural intervertebral discs. This provides some level of compressibility and formability during impact loads, thereby decreasing the chance of subsidence and other undesired consequences. However, an implantable device formed entirely of materials having properties like those of natural bone or natural intervertebral discs may have some drawbacks. For example, portions of the implantable device may yield when bone anchors are driven into bores formed in the implantable device. This may lead to loosening of the implantable device over time. One approach to address loosening around the bone anchors is to form the implantable device of a rigid material, such as a metal material. However, metal materials may not have properties that favorably interface with the bearing endplates of the vertebrae. The implantable device disclosed herein includes a weight bearing spacer that supports a patient, but also includes anchor bores that are resistant to yielding and deformation.

Figure 3:
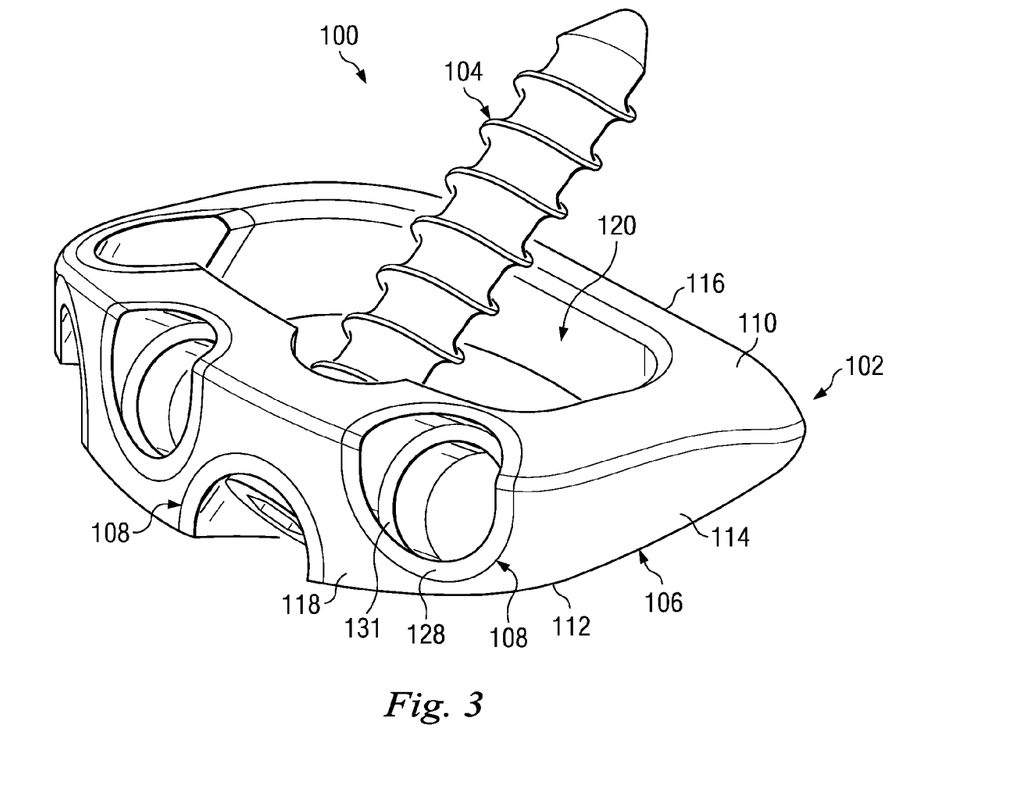
FIG. 3 is an illustration of a perspective view of one exemplary embodiment of the implantable device shown in FIG. 2.
Figure 4:
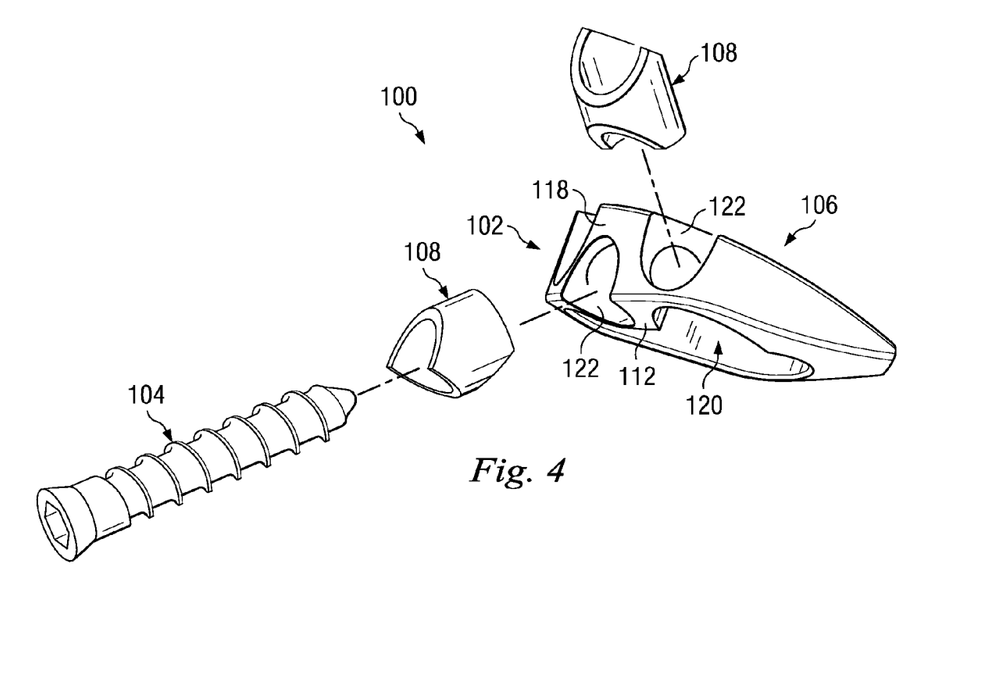
FIG. 4 is an illustration of a partially exploded view of the exemplary implantable device shown in FIG. 3.

FIGS. 3 and 4 show the implantable device 100 in greater detail. FIG. 3 shows a perspective view of the implantable device 100, while FIG. 4 shows an exploded view. Referring now to both FIGS. 3 and 4, the implantable device 100 includes a composite interbody spacer 102, and one or more bone anchors 104. The interbody spacer 102 may include a first portion 106 formed of a first material and a second portion 108 formed of a second material. The first portion 106 may include an upper surface 110, a lower surface 112, side surfaces 114, a rear surface 116 and a front surface 118. The upper and lower surfaces 110, 112 may be configured to interface with the bearing endplates of the upper and lower vertebrae 14, 16 as shown in FIG. 2, while the side, rear, and front surfaces 114, 116, 118 extend between the upper and lower surfaces 110, 112. A hollow region 120 may allow placement of bone growth materials, such as allograft to promote bonding and fusion of the implantable device 100 to the adjacent vertebrae.

In the embodiment shown, the upper and lower surfaces 110, 112 are relatively smooth surfaces. However, in other embodiments, the upper and lower surfaces include bone engaging features configured to reduce slipping or movement of the interbody spacer 102 relative to the vertebrae 14, 16. Examples of bone engaging features are discussed herein relative to other implantable device embodiments.

The front surface 118 includes bores 122 (best seen in FIG. 4) that extend through the first portion 106 from the front surface 118 to the hollow region 120. In the embodiment shown, the bores 122 are formed at an angle and also extend inwardly from the upper and lower surfaces 110, 112. In this exemplary embodiment, the front surface 118 includes four bores 122.

The first portion 106 bears the weight of and interfaces with the endplates of the vertebrae 14, 16. In order to minimize subsidence and maximize compatibility, the first portion 106 may be formed of a material less rigid than a material of the second portion 108. In some exemplary embodiments, the first portion 106 is formed of a biocompatible polymer material that may include properties similar to those of natural bone or natural intervertebral discs. Examples of first portion materials include, but are not limited to, reinforced or non-reinforced polymers, carbon-reinforced polymer composites, polymers from the Polyaryletherketone (PAEK) family, including PEK, PEEK, PEKK, and PEKEKK, and PAEK composites. In some embodiments, the first portion may be formed of shape-memory alloys, titanium, titanium alloys, cobalt chrome alloys, stainless steel, ceramics and combinations thereof. In other embodiments, the first portion 106 may be formed of a shape memory material or a super elastic material.

Figure 5:
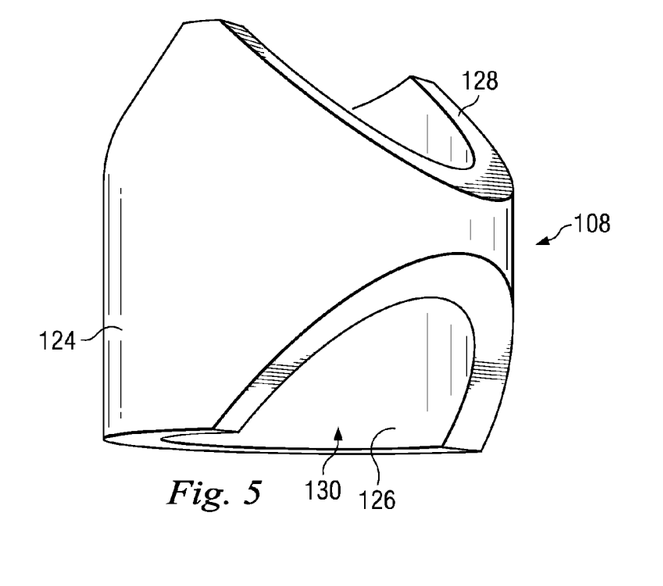
FIG. 5 is an illustration of a portion of the exemplary implantable device shown in FIG. 3.

The second portion 108, shown best in FIG. 4 and in FIG. 5, is formed of a material different than the first portion 106, and is configured to reinforce the bores 122 and interface with the bone anchors 104. The material may be more rigid than the material of the first portion 106 and may be better able to withstand loads applied during implantation of the implantable device 100. In some embodiments, the second portion 108 may be formed of shape-memory alloys, titanium, titanium alloys, cobalt chrome alloys, stainless steel, ceramics and combinations thereof. In other embodiments, the second portion 108 may be formed of a shape memory material, a super elastic material, or relatively rigid polymers or composites. In one embodiment, the second portion 108 is formed of a metal material such as titanium, and the first portion 106 is formed of a polymer from the PAEK family, such as PEEK.

In the embodiment shown, the second portion 108 is formed of one or more tubular inserts having an outer surface 124, an inner surface 126, and edges 128. When implanted, the second portion 108 receives the bone anchors 104 and reinforces the bores 122 in the first portion 106 to resist yielding or creep about the bone anchors 104. This stabilizes the implantable device 100 between the upper and lower vertebrae 14, 16 and also allows the weight bearing first portion 106 to interface with the upper and lower vertebral bodies.

The outer surface 124 may be tapered, thereby providing a conical or frustum shape to the second portion 108. It also may be roughened, or may have surface features that help secure the second portion 108 in place in the bore 122 of the first portion 106. As shown in FIG. 3, the edges 128 may be configured to lie flush with the front surface 118 and the upper or lower surfaces 110, 112 of the first portion 106. It should be apparent that in other embodiments, the second portion 108 may penetrate only a single surface, rather than more than one surface. The inner surface 126 defines a bore 130 configured to interface with the bone anchor 104 in a manner known in the art, and may include a tapering surface or other surface features known in the art. In some embodiments, the interface may include a shoulder 131 as shown in FIG. 3. The exploded view in FIG. 4 shows only two second portions 108 exploded from the first portion 106.

The bone anchors 104, only one of which is shown in FIG. 3, attach the interbody spacer 102 to the vertebral bodies 14, 16. In this exemplary embodiment, the bone anchors 104 are bone screws. However, other bone anchors are contemplated. The bone anchors 104 extend through the front surface 118 and/or upper or lower surfaces 110, 112 and extend out of the hollow region 120 and into the bearing endplates of the vertebrae 14, 16, thereby securely locating the interbody spacer 102 entirely within the disc space. Although only a single bone anchor 104 is shown, it is contemplated that a bone anchor would be used in each bore 122. In this exemplary embodiment, the interbody spacer 102 includes four bores 122—two angled to allow bone anchors 104 to attach to an upper vertebral endplate and two angled to allow bone anchors 104 to attach to a lower vertebral endplate. This allows the bone anchors 104 to penetrate the bearing endplates of the vertebral bodies.

As shown in FIG. 3, when the second portion 108 is embedded within the first portion 106, the bone anchor 104 extends through both the second portion bore 130 and the first portion bore 122. Because the bone anchor interfaces directly with the rigid second portion 108, it does not pull through and does not cause significant elastic yielding over time. The second portion 108, having a much larger surface area than the bone anchor 104, interfaces with the less rigid material of the first portion 106, and helps secure the first portion 106 in place in contact with the vertebrae 14, 16.

Figure 18:
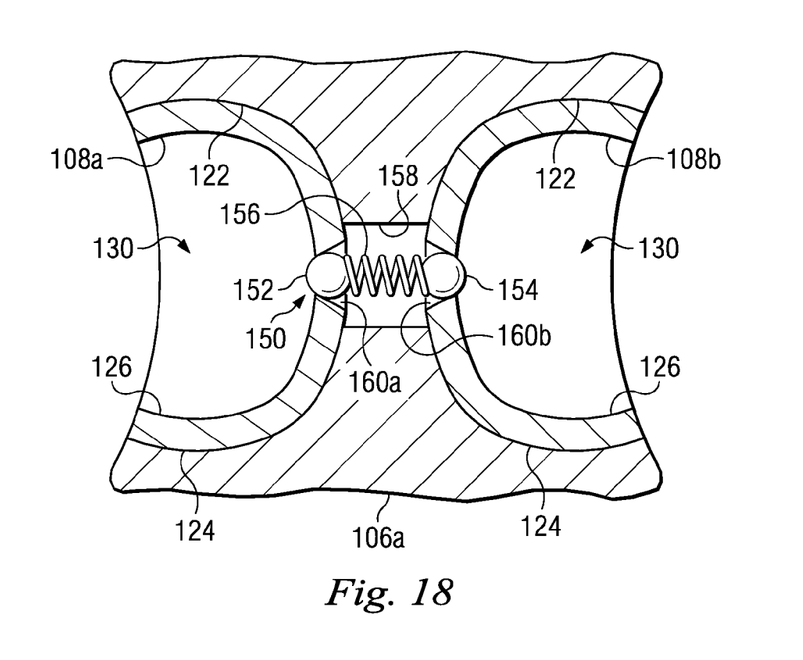
FIG. 18 is an illustration of a portion of an exemplary locking mechanism.

Some exemplary embodiments include a locking mechanism to inhibit bone anchor back-out. One exemplary embodiment of a locking mechanism is shown in FIG. 18. The locking mechanism, referenced herein by the reference numeral 150, includes a first and a second protruding portion 152, 154 and a spring 156. In this exemplary embodiment, the first and second portions 106, 108 may be modified to cooperate with the locking mechanism 150 to inhibit back out of the bone anchors 104. As used herein, the modified first and second portions are referenced as first portion 106a and second portions 108a and 108b. As described above, the first portion 106a includes bores 122 that receive a part of the second portion. Here, the first portion 106a includes a channel 158 connecting two of the bores 122 together. The channel 158 may be formed to extend substantially normal from a line tangent to the inner surface of the bore 122, or alternatively, may extend at an angle. The channel 158 may be sized with a diameter or width greater than the diameter or width of one of the first and second protruding portions 152, 154 and greater than the diameter of the spring 156.

Each second portion 108a-b includes a passage 160a-b that extends through the outer surface 124 and the inner surface 126 of each of the second portions 108a-b. The passages 160a-b may be sized so that a first part of the first and second protruding portions 152, 154 protrudes into the bore 130, but that the remaining part does not. As shown in FIG. 18, the spring 156 biases the first and second protruding portions 152, 154 so that they protrude into the bore 130 of each second portion 108a.

When the bone anchor 104 is introduced into the bore 130 it advances until a head portion on the bone anchor 104 pushes against one of the protruding portions 152, 156 and physically forces it to retract against the spring into the passage 160. Once the bone anchor 104 passes the protruding portion, the spring 160 may cause the protruding portion to retake its place so that it protrudes into the bore 130 behind the bone anchor 104. The protruding portion 152, 156 may cooperate with the bone anchor 104 to inhibit screw backout by physically blocking the bone anchor 104 from moving back out of the bore 130.

In some exemplary embodiments, the bone anchor 104 includes a channel or divot configured to receive the protruding portion 152, 154 so that the bone anchor 104 need not advance completely past the protruding portions 152, 154 before inhibiting back-out. In the exemplary embodiment shown, the protruding portions 152, 154 are round balls. However, they may be shaped as cylinders, cones, or other shapes.

The locking mechanism 150 may be placed within the implantable device by first inserting one second portion 108a into the first portion 106a. The passage 160a may be aligned with the channel 158. Then the protruding portion 152, the spring 156, and the protruding portion 154 may be inserted into the channel 158, in that order. Finally, the second portion 108b may be introduced into the bore 122 in the first portion 106a until the passage 160b align with the channel 158.

It should be noted that any other locking mechanism may be used to inhibit screw back-out. For example, in alternative embodiments, the locking mechanism may include a locking ring as described in co-pending U.S. patent application Ser. No. 11/695,939, having the same filing date as the present application, incorporated herein in its entirety by reference. In other exemplary embodiments, the locking mechanism may include a faceplate as described in co-pending U.S. patent application Ser. No. 11/695,883, having the same filing date as the present application, incorporated herein in its entirety by reference. Yet other locking mechanisms are contemplated. Further, it is contemplated that locking mechanisms may be employed on any of the exemplary embodiments disclosed herein.

Figures 6, 7:
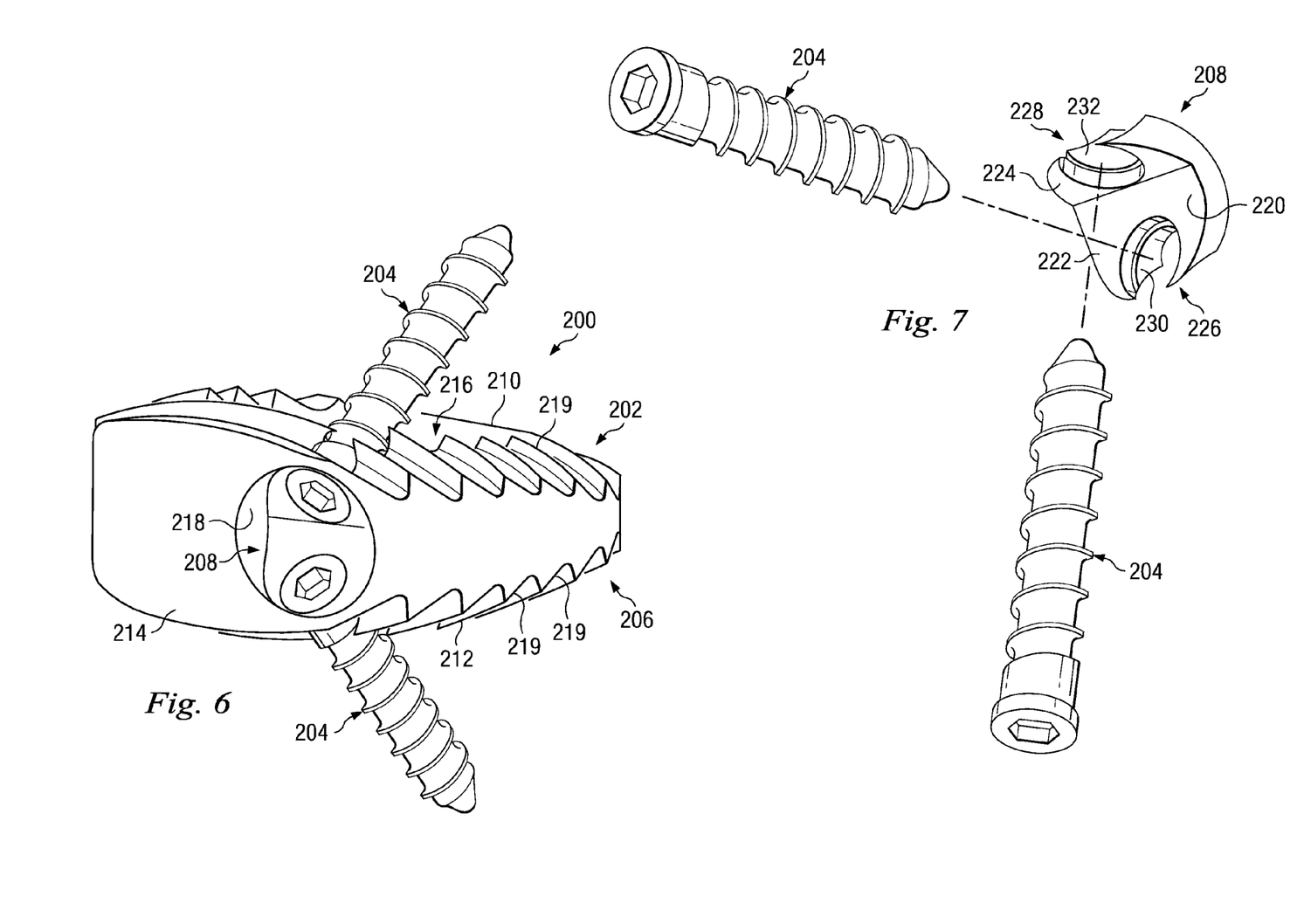
FIG. 6 is an illustration of a perspective view of another exemplary embodiment of an implantable device.
FIG. 7 is an illustration of an exploded view of a part of the exemplary implantable device shown in FIG. 6.
Figure 8:
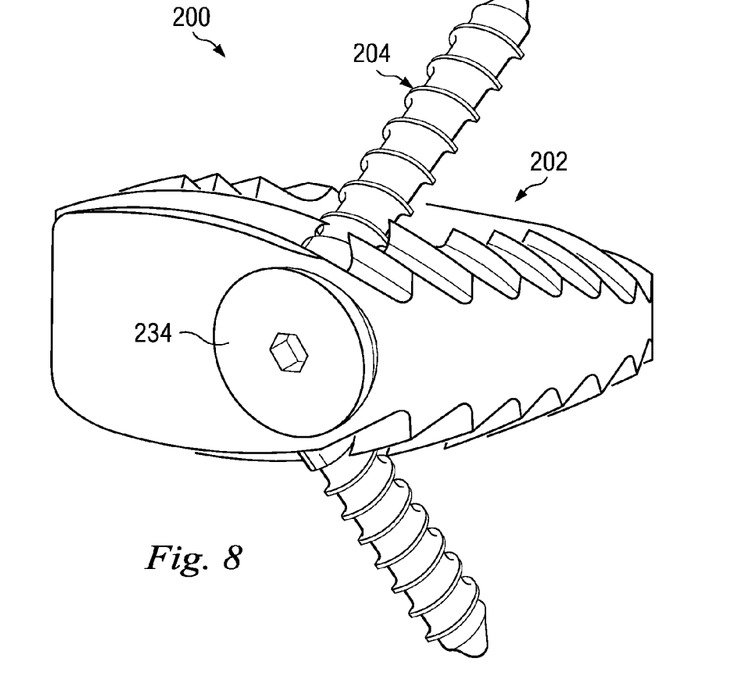
FIG. 8 is an illustration of a perspective view of the exemplary implantable device shown in FIG. 5 with a locking mechanism.

FIGS. 6-8 show another exemplary embodiment of an implantable device, referenced herein by the numeral 200. In this exemplary embodiment, the implantable device 200 includes an interbody spacer 202 and bone anchors 204. The interbody spacer 202 in this exemplary embodiment includes a first portion 206 formed of a relatively less rigid material and a second portion 208 formed of a relatively more rigid material. The first and second portions 206, 208 may be formed of the same or similar materials to the first and second portions described above with reference to FIGS. 3-5. In addition, the implantable device 200, as well as any embodiment disclosed herein, may include any of the features of any of the other embodiments disclosed herein, and to reduce repetition, many of the features and advantages of the different embodiments will not be reiterated.

Here the first portion 206 of the interbody spacer 202 includes an upper surface 210, a lower surface 212, a front surface 214, and a hollow region 216. The front surface 214 includes a bore 218 formed therein extending from the front surface 214 to the hollow region 216.

In the embodiment shown, the upper and lower surfaces 210, 212 include bone engaging features 219 configured to reduce slipping or movement of the interbody spacer 202 relative to adjacent vertebrae. In the exemplary embodiment shown, the bone engaging features 219 are angled teeth that permit introduction into the disc space, but also restrict removal.

The second portion 208, shown best in FIG. 7, is sized to fit at least partially within and reinforce the bore 218 in the first portion 206. In the embodiment shown, the second portion 208 fits entirely within the bore 218, although it may protrude out of the bore 218 in other embodiments. The second portion 208 includes a base surface 220 and first and second angled surfaces 222, 224. Bone anchor receiving bores 226, 228 extend through the second portion 208 at the respectively first and second angled surfaces 222, 224. In the embodiment shown, the bores 226, 228 are not entirely closed bores, however, in alternative embodiments, the bores 226, 228 are enclosed. The bores 226, 228 each have an inner surface 230, 232 formed with surface features, such as shoulders to interface with the bone anchors 204 in a manner known in the art.

In this exemplary embodiment, the surfaces 222, 224 angle to correspond to the desired angle of the bone anchors 204, extending from the interbody spacer 202. Thus, in this embodiment, the first and second bores 226, 228 are substantially perpendicular to the planes formed by the respective angled surfaces 222, 224. Here, the first and second bores 226, 228 are vertically spaced so that one is above the other when in an implanted orientation as shown in FIG. 6, however, other configurations are contemplated.

As described above with reference to the implantable device 100, the bone anchors 204 extend through the front surface 214 and out the hollow region 216 or alternatively, through the front surface 214 and the upper or lower surfaces 210, 212. They extend into the bearing endplates of the vertebrae, thereby securely locating the interbody spacer 102 entirely within the disc space. In this exemplary embodiment, two bone anchors 104 are shown, however, it is contemplated that additional bone anchors, through additional bores in the first portion may be employed.

As shown in FIG. 6, when the second portion 208 is embedded within the first portion 206, each bone anchor 204 extends through one of the second portion bores 226, 228 and through the first portion bore 218. Because the bone anchor 204 interfaces directly with the rigid second portion 208, it does not pull through and does not cause significant elastic yielding over time. The second portion 208, having a much larger surface area than the bone anchor 204, interfaces with and reinforces the less rigid material of the first portion 206, and helps secure the first portion 206 in place in contact with the vertebral bodies.

FIG. 8 shows the implantable device 200 with a locking mechanism 234 to inhibit screw back-out. In this exemplary embodiment, the locking mechanism 234 is a plate having a threaded post (not shown) configured to be driven into a corresponding receiving hole on the second portion 208 or elsewhere in a manner known in the art. Although not shown in FIG. 7, the receiving hole may be formed in the base surface 220, although other locations are contemplated. The implantable device 200 is shown having a single bore 218 and a single second portion 208 however, other embodiments have one or more additional bores 218 and additional second portions 208 that may receive additional bone anchors 204.

Figure 9:
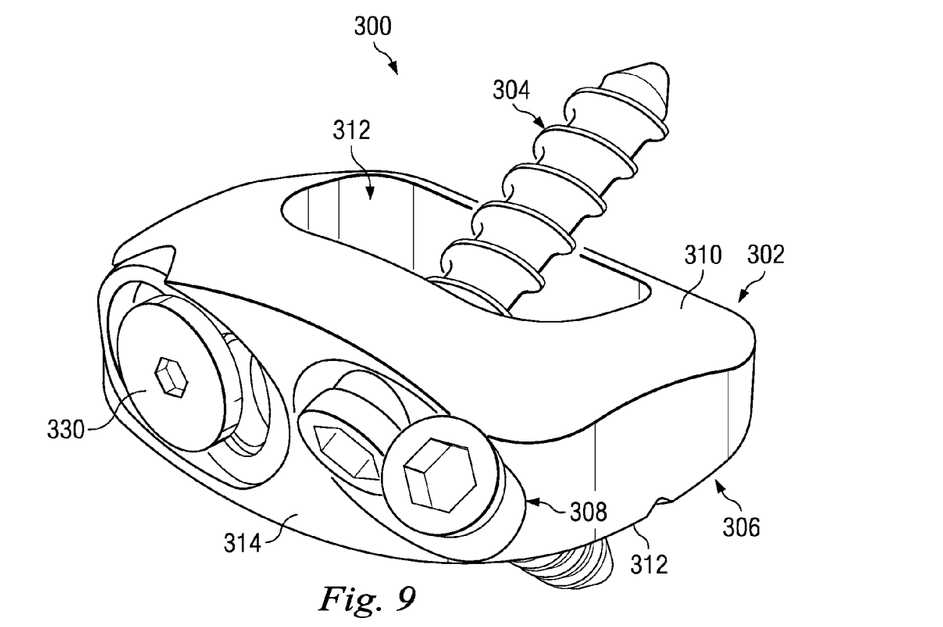
FIG. 9 is an illustration of a perspective view of another exemplary embodiment of an implantable device.
Figures 10, 11:
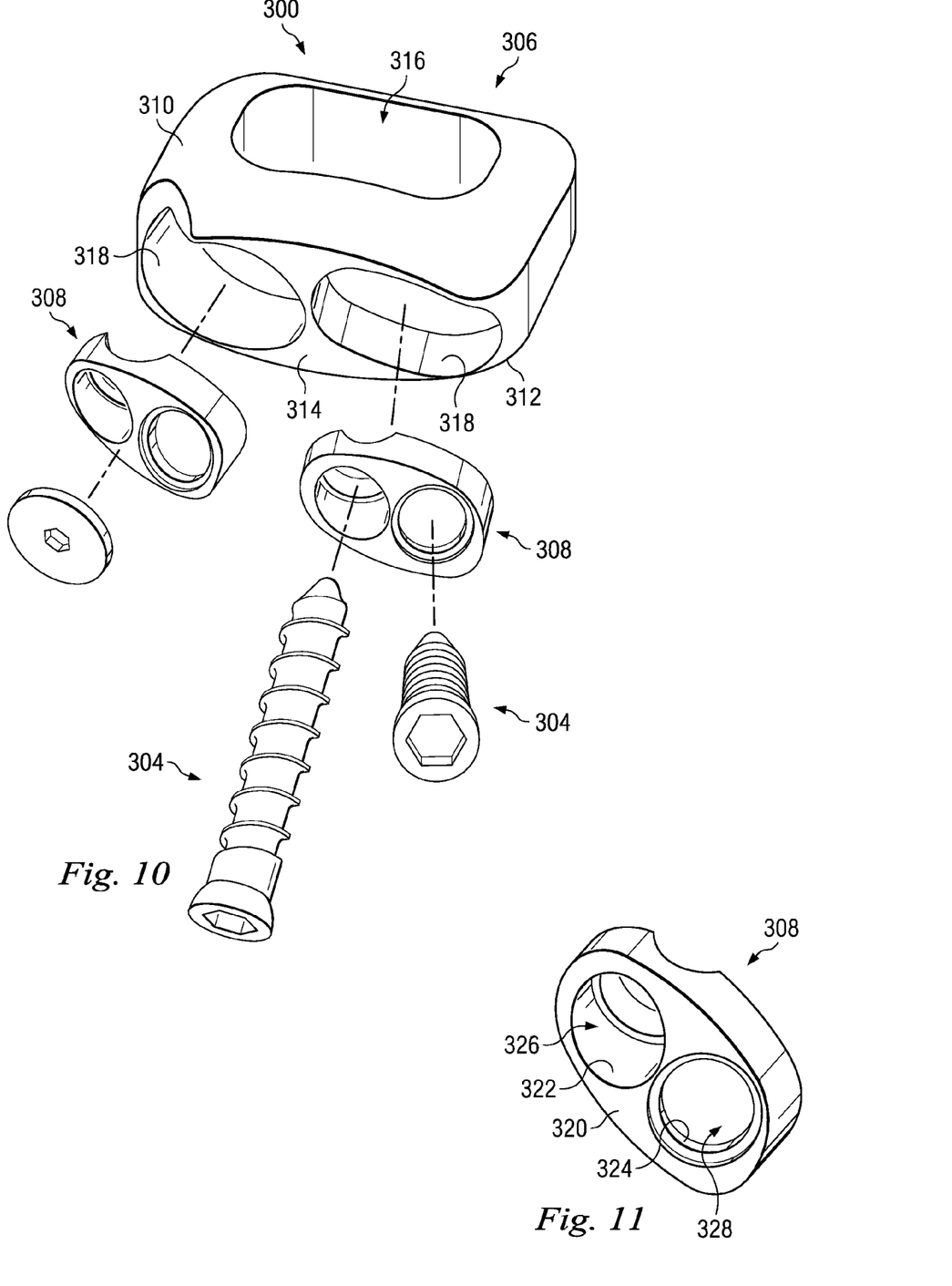
FIG. 10 is an illustration of an exploded view of the exemplary implantable device shown in FIG. 9.
FIG. 11 is an illustration of a portion of the exemplary implantable device shown in FIG. 9.

FIGS. 9 and 10 show yet another exemplary implantable device, referenced herein by the numeral 300. In this exemplary embodiment, the implantable device 300 includes an interbody spacer 302 and bone anchors 304. The interbody spacer 302 in this exemplary embodiment includes a first portion 306 formed of a relatively less rigid material and a second portion 308 formed of a relatively more rigid material. The first and second portions 306, 308 may be formed of the same or similar materials as the first and second portions described above with reference to FIGS. 3-5.

Here, the first portion 306 of the interbody spacer 302 includes an upper surface 310, a lower surface 312, a front surface 314, and a hollow region 316. The front surface 314 includes at least one bore 318 formed therein extending from the front surface to the hollow region 316. The bore 318 also may intersect with the upper and lower surfaces 310, 312. Here, the bore 318 is an elongated oval shape formed so that the major axis of the oval is angled relative to the upper and lower surfaces 310, 312.

The second portion 308, shown best in FIG. 11, is sized to fit at least partially within and reinforce the bore 318 in the first portion 306. In the embodiment shown, the second portion 308 fits entirely within the bore 318, yet in other embodiments, it protrudes out of the bore 318. The second portion 308 comprises an elongated shape that matches the shape of the bore 318 and includes a front surface 320 having first and second inner surfaces 322, 324 respectively defining first and second bone anchor receiving bores 326, 328 extending therethrough. While the second portion 208 described above had two bores in a vertical orientation, the second portion 308 has two bores spaced horizontally. The bores 326, 328 extend from the front surface at angles desired for the bone anchors, and the inner surfaces 322, 324 may include surface features to interface with the bone anchors in a manner known in the art.

As described above with reference to other embodiments of the implantable devices, the bone anchors 304 extend through the front surface 314 of the first portion 306 and out the hollow region 316 and into the bearing endplates of the vertebrae, thereby securely locating the interbody spacer 302 entirely within the disc space. In this exemplary embodiment, two bone anchors 304 are shown, however, it is contemplated that additional bone anchors through additional bores in the first portion 306 may be employed.

As shown in FIG. 9, when the second portion 308 is embedded within the first portion 306, the bone anchors 304 extend through one of the bores 226, 228 and through the first portion bore 318. Because the bone anchor 304 interfaces directly with the rigid second portion 308, it does not pull through and does not cause significant elastic yielding over time. The second portion 308, having a much larger surface area than the bone anchor 304, interfaces with and reinforces the less rigid material of the first portion 306, and helps secure the first portion 306 in place in contact with the vertebral bodies. An exemplary locking mechanism 330 shown in FIG. 9 may be employed to inhibit screw back-out.

Yet another embodiment of an implantable device is shown in FIGS. 12-15, referenced herein by the numeral 400. In this exemplary embodiment, the implantable device 400 includes an interbody spacer 402 and bone anchors (not shown). The exemplary interbody spacer 402 includes a first portion 406 formed of a relatively less rigid material and a second portion 408 formed of a relatively more rigid material, as described above with reference to the other embodiments.

Figure 12:
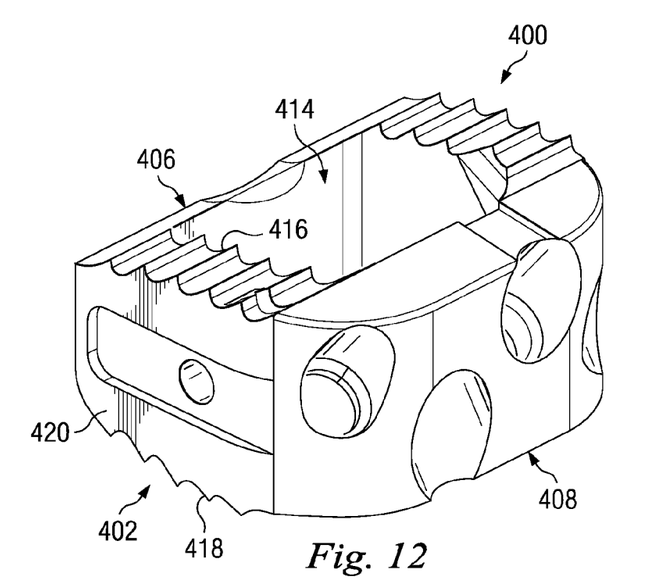
FIG. 12 is an illustration of a perspective view of another exemplary embodiment of an implantable device.

Here, the first and second portions 406, 408 cooperate to form the bearing portions of the interbody spacer 402. For example, instead of being embedded in the first portion 406, the second portion 408 connects to the first portion 406 and interfaces with the endplates of the adjacent vertebrae. The first portion 406 is a U-shaped element having a first end 410 and a second end 412 (shown in FIG. 13) that form end surfaces, with the second portion 408 extending from one of the first and second ends 410, 412 to the other. Accordingly, the first and second portions 406, 408 together define a hollow region 414.

Figure 13:
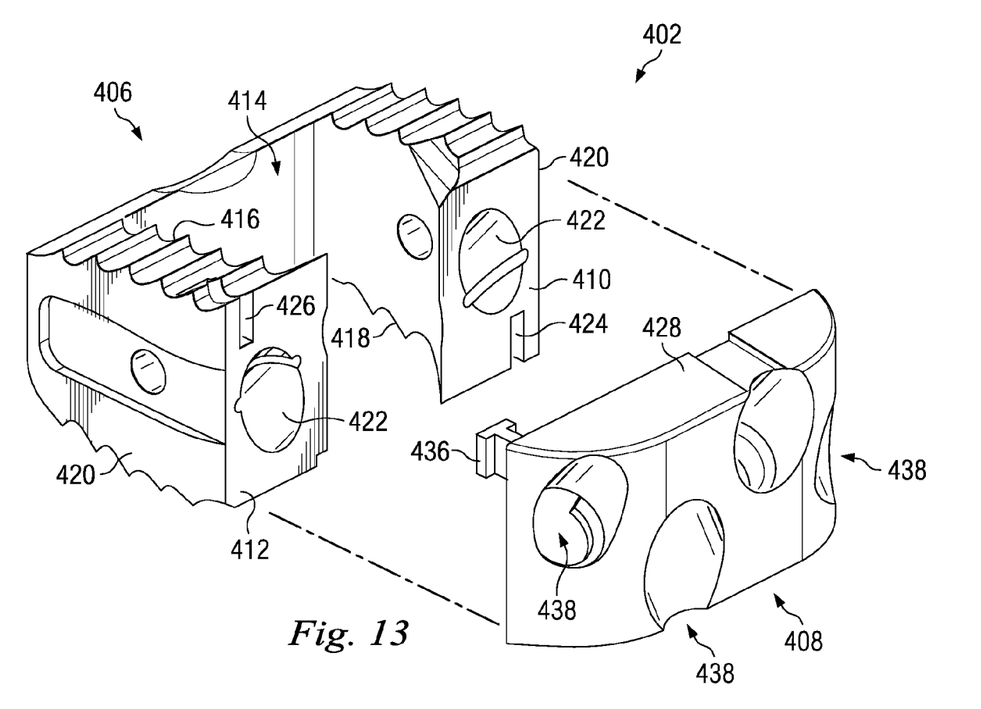
FIG. 13 is an illustration of an exploded view of the exemplary implantable device shown in FIG. 12.

The first portion 406 in this embodiment includes an upper surface 416, a lower surface 418, side surfaces 420, and the ends 410, 412. The upper and lower surfaces 416, 418 may be configured to interface with the bearing endplates of upper and lower vertebrae, while the side surfaces 420 and the ends 410, 412 extend between the upper and lower surfaces 416, 418. Here, the upper and lower surfaces 416, 418 are shown with bone engaging features configured to reduce slipping or movement of the interbody spacer 102 relative to the vertebrae 14, 16.

The first and second ends each include a bore 422 (best seen in FIG. 13) that extends through the upper or lower surfaces 416, 418. In the embodiment shown, the bores 422 are sized to receive a part of a bone anchor and are formed at an angle that allows the bone anchors to penetrate the upper and lower endplates of the vertebrae.

In addition, in this exemplary embodiment, the first end 410 includes a connecting feature 424 as a first slot formed into the end surface of the first end 410, extending upwardly from the lower surface 418 into the body of the first portion 406. A similar second connecting feature 426 as a second slot in the end surface of the second end 412 extends downwardly from the upper surface 416. In this exemplary embodiment, the connecting features are T-shaped slots sized to mate with protruding fasteners forming a part of the second portion 408.

Figure 14:
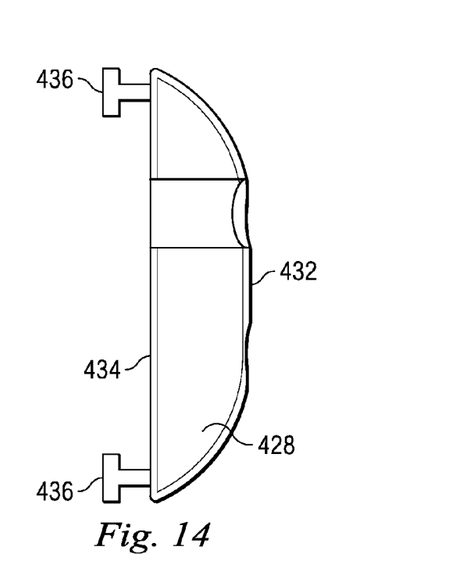
FIG. 14 is an illustration of a top view of a portion of the exemplary implantable device shown in FIG. 12.
Figure 15:
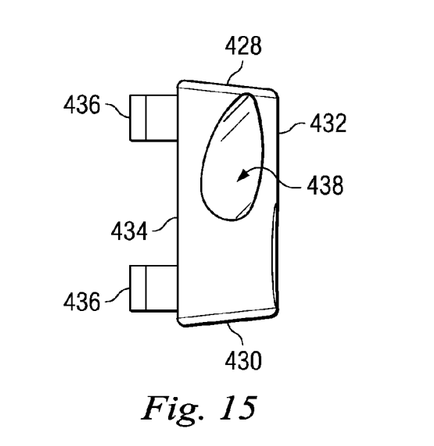
FIG. 15 is an illustration of a side view of a portion of the exemplary implantable device shown in FIG. 12.

The second portion is described in greater detail with reference to FIGS. 13-15. FIG. 14 shows a top view and FIG. 15 shows a side view. Having a height similar to that of the first portion 106, the second portion 408 also may bear weight of and directly contact the adjacent vertebrae. The second portion 408 includes an upper and lower surface 428, 430, a front surface 432, and an interfacing surface 434.

Protruding fasteners 436 extend from the interfacing surface 434 and are configured to fit within the first and second connecting features 424, 426 of the first portion 406. As best seen in FIGS. 14 and 15, the protruding fasteners are T-shaped, with one being disposed to extend from adjacent the upper surface 428 and one being disposed to extend from adjacent the lower surface 430.

Bores 438 sized to receive screw anchors extend through the second portion 408 from the front surface 432 to the interfacing surface 434. In this exemplary embodiment, there are four bores 438. Two of which align with the bore 422 in the first portion 406 so that a bone anchor extending through the bores passes through both the first and second portions 406, 408. The other two bores in this exemplary embodiment do not align with the first portion 406, and bone anchors extending through these bores protrude from the interfacing surface 434 of the second portion 408 through the hollow region 414 and into the vertebral endplates.

Because all the bone anchors interface directly with the rigid second portion 408, they do not pull through and do not cause significant yielding over time. The second portion 408, being formed of a more rigid material, supports the bone anchors and interfaces with the less rigid material of the first portion 206 to help secure the first portion 206 in place in contact with the vertebral bodies.

As described above, the interbody spacer 402 may be shaped to cooperate with any known locking mechanism that inhibits screw back-out. Some embodiments of the second portion may be configured to fit the faceplate or ring mechanisms described above.

Figure 16:
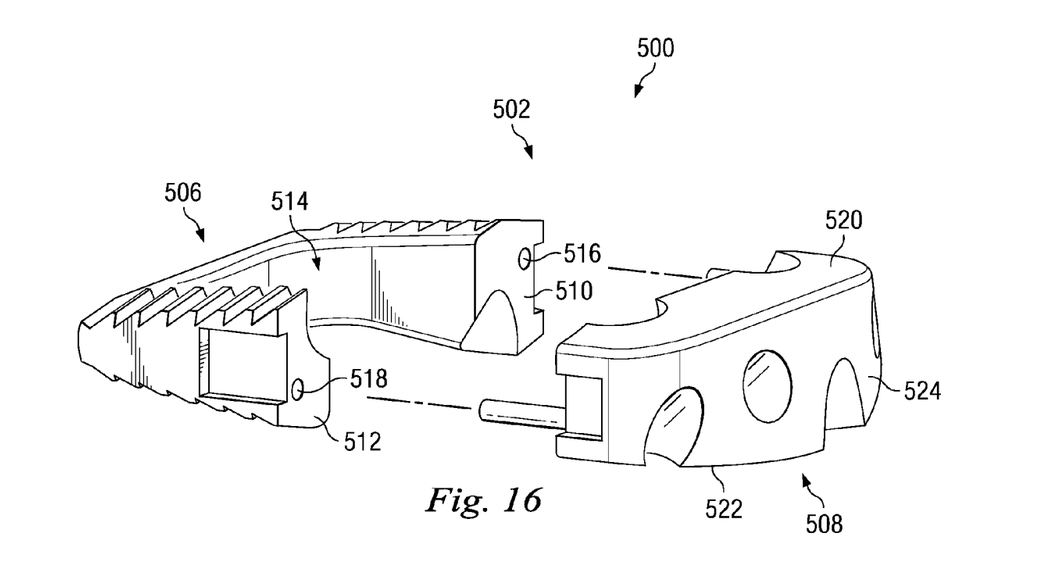
FIG. 16 is an illustration of an exploded perspective view of another exemplary embodiment of an implantable device.
Figure 17:
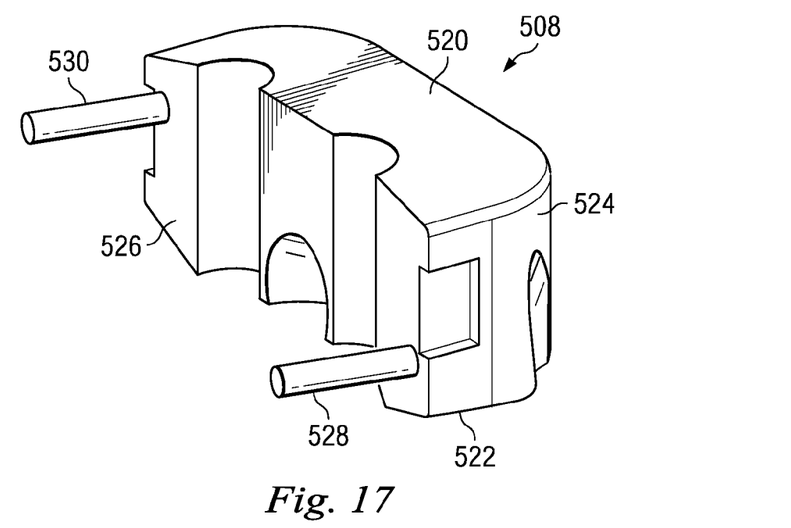
FIG. 17 is an illustration of a portion of the exemplary implantable device shown in FIG. 16.

Yet another exemplary embodiment of an implantable device is shown in FIGS. 16 and 17, referenced herein by the numeral 500. In this exemplary embodiment, the implantable device 500 includes an interbody spacer 502 and bone anchors (not shown). The interbody spacer 502 in this exemplary embodiment includes a first portion 506 formed of a relatively less rigid material and a second portion 508 formed of a relatively more rigid material as described above.

As with the implantable device 400, the first and second portions 506, 508 cooperate to form the bearing portions of the interbody spacer 502, with the second portion 208 connecting to the U-shaped first portion 506 and together defining a hollow region 514.

The first portion 506 in this embodiment includes first and second ends 510, 512, respectively having surfaces that include a first and a second connecting feature 516, 518 extending therethrough, into the first portion 506. In this exemplary embodiment, the connecting features 516, 518 are bores formed into the surfaces at the ends 510, 512 of the first portion 506.

The second portion 508 has a height similar to that of the first portion 506 and therefore, also may bear weight of and directly contact the adjacent vertebrae. The second portion 508 includes an upper and lower surface 520, 522, a front surface 524, and an interfacing surface 526.

Protruding fasteners 528 extend from the interfacing surface 522 and are configured to fit within the first and second connecting features 516, 518 of the first portion 506. Here, the protruding fasteners 528 are cylindrical protrusions, however it is contemplated that the protruding fasteners could be tapered and would connect to the first portion though a taper-lock. Alternatively, they may include features that allow the first and second portions to snap together.

Bores 530 sized to receive screw anchors extend through the second portion 508 from the front surface 524 to the interfacing surface 526. In this exemplary embodiment, the second portion 508 alone includes screw anchor bores 530, while the first less rigid first portion 506 secures to the second portion 508.

When the protruding fasteners 528 of the second portion are embedded within the connecting features 516, 518 of the first portion 506, bone anchors may be introduced to extend through the bores 530. Here, all the bone anchors interface directly with the rigid second portion 508 and do not pass through the first portion 506. Because of this, they do not pull through and do not cause significant elastic yielding over time. The second portion 508, being formed of a more rigid material, supports the bone anchors and interfaces with the less rigid material of the first portion 506 to help secure the first portion 506 in place in contact with the vertebral bodies. It should be noted that in some alternative embodiments, the protruding fasteners 528 are formed on the less rigid first portion 506 and extend into or interface with the second portion 508.

Although described as interfacing with the vertebral endplates, in some alternative embodiments, the second portion height is less than that of the first portion height. In these embodiments, the second portion 408, 508 may be sized and configured to not bear weight of the vertebrae, with it being supported entirely by the less rigid first portion 406, 506.

In other alternative embodiments, the first portion itself defines the hollow region the but the second portion still attaches to the first portion using connecting features in a manner disclosed in FIGS. 13 and 16.

A method of implantation is described below with reference to the first embodiment of the implantable device 100 disclosed herein. However, the method of implantation is intended to be equally applicable to all the disclosed embodiments.

The interbody spacers may be implanted between the vertebrae 14, 16 using any common approach, including an anterior approach, a posterior approach, a posterior transforaminal approach, a far lateral approach, a direct lateral approach, among others. According to at least one of these approaches, an incision, such as a midline incision, may be made in the patient's back and some or all of the affected disc and surrounding tissue may be removed via the foramina.

The endplate surface of the vertebra 14 may be milled, rasped, or otherwise resected to match the profile of the upper surface 110 of the interbody spacer 102, to normalize stress distributions on the endplate surface of the vertebra 14, and/or to provide initial fixation prior to bone ingrowth. The preparation of the endplate of vertebra 14 may result in a flattened surface or in surface contours such as pockets, grooves, or other contours that may match the bone engaging features 120 on the upper surface 110. The endplate of the vertebra 16 may be similarly prepared to engage the lower surface 112 of the interbody spacer 102 to the extent allowed by the exiting nerve root and the dorsal root ganglia. In some procedures, the natural facet joints of vertebrae 14, 16 may be trimmed or removed to provide access to the disc space.

The interbody spacer 102, with both the first and second portions, may then be placed in the prepared disc space between the adjacent vertebrae 14, 16 so that the upper and lower surfaces 110, 112 contact bearing endplates of the vertebral bodies. This may include orienting the interbody spacer 102 so that at least a part of the weight of the patient will be carried by the less rigid first portion of the interbody spacer 102. Once positioned, one of the bone anchors 104 may be introduced through one of the bores 122 in the second portion 108 of the interbody spacer 102, and then rotated to engage with and advance into one of the vertebral endplates. As the bone anchor 104 advances through the aperture bore 122, the head portion 140 of the bone anchor 104 engages against the rigid second portion 108 of the interbody spacer 102, driving it into and securely attaching it the first portion 106. Thus, the second portion 108 cooperates to secure the first portion 106 in place.

In some embodiments, the implantable devices disclosed herein or individual components of the implantable devices are constructed of solid sections of bone or other tissues. Further, in some circumstances, it is advantageous to pack the hollow region of any of the interbody spacers with a suitable osteogenetic material or therapeutic composition. Osteogenic materials include, without limitation, autograft, allograft, xenograft, demineralized bone, synthetic and natural bone graft substitutes, such as bioceramics and polymers, and osteoinductive factors. A separate carrier to hold materials within the device can also be used. These carriers can include collagen-based carriers, bioceramic materials, such as BIO-GLASS®, hydroxyapatite and calcium phosphate compositions. The carrier material may be provided in the form of a sponge, a block, folded sheet, putty, paste, graft material or other suitable form. The osteogenetic compositions may include an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agents, separately or held within a suitable carrier material. A technique of an embodiment of the invention is to first pack the interior of the interbody spacer with material and then place it within the disc space.

In one exemplary embodiment, the hollow region may be filled with a radiopaque material, such as, for example, a cement including barium sulfate. In another exemplary embodiment, the first portion itself may be formed of and/or may include radiopaque materials. For example, the first portion may include wires forming a part of the upper, lower or side surfaces. Therefore, after the surgery, the prosthetic device 100 can be viewed and analyzed, if necessary.

Access to the surgical site may be through any surgical approach that will allow adequate visualization and/or manipulation of the bone structures. Example surgical approaches include, but are not limited to, any one or combination of anterior, antero-lateral, posterior, postero-lateral, transforaminal, and/or far lateral approaches. Implant insertion can occur through a single pathway or through multiple pathways, or through multiple pathways to multiple levels of the spinal column. Minimally invasive techniques employing instruments and implants are also contemplated.

It is understood that all spatial references, such as "top," "inner," "outer," "bottom," "left," "right," "anterior," "posterior," "superior," "inferior," "medial," "lateral," "upper," and "lower" are for illustrative purposes only and can be varied within the scope of the disclosure.

While embodiments of the invention have been illustrated and described in detail in the disclosure, the disclosure is to be considered as illustrative and not restrictive in character. All changes and modifications that come within the spirit of the invention are to be considered within the scope of the disclosure.

We claim:

1. A composite interbody spacer comprising:
 a first portion being formed of a first material, the first portion shaped and sized for placement in an intervertebral disc space between an upper vertebral body and a lower vertebral body to separate the upper and lower vertebral bodies at a distance that provides proper spinal column function, the first portion being configured as a load bearing portion, the first portion having an upper surface shaped and sized to bear loads applied from the upper vertebral body and having a lower surface shaped and sized to bear loads applied from the lower vertebral body, the first portion having an outwardly facing front surface and having a rear surface opposing the front surface, the front surface having a first bore formed therein, the first bore having a surface shape and wherein the first bore extends at an oblique angle relative to the front surface; and
 a second portion being formed of a second material, at least a portion of the second portion having an outer surface shape closely matching the surface shape of the first bore and being at least partially disposed within the first bore in a manner that reinforces the first bore and in a manner to interface with a bone anchor extending through the first bore, the second portion including a second bore formed therein that is at least partially disposed within the first bore in a manner that a bone anchor can extend through the first and second bores, the second bore having an outer surface,
wherein the outer surface of the second bore forms a continuous perimeter adjacent to the surface of the first bore such that the second portion substantially resists elastic yielding.

2. The spacer of claim 1, wherein the second portion includes an unthreaded second bore formed therein that is at least partially disposed within the first bore in a manner that a bone anchor can extend through the first and second bores.

3. The spacer of claim 1, wherein the first portion is a polymer and the second portion is a metal.

4. The spacer of claim 3, wherein the first portion is formed of a member of the polyaryletherketone family.

5. The spacer of claim 1, wherein the first portion includes a hollow region.

6. The spacer of claim 1, wherein the second portion is a tubular sleeve.

7. The spacer of claim 6, wherein the tubular sleeve includes an inner shoulder.

8. The spacer of claim 1, wherein the second portion is embedded entirely within the first bore.

9. The spacer of claim 1, wherein the second portion includes a second bore and a third bore formed therein and being partially disposed within the first bore in a manner that a first bone anchor can extend through the first and second bores and a second bone anchor can extend through the first and third bores.

10. The spacer of claim 9, wherein the second and third bores extend at different angles through the second portion.

11. An implantable device including:
the composite interbody spacer of claim 1; and
a bone anchor extending through the first bore and interfacing with the second portion, wherein the front surface of the first portion has a first height measured between the first upper and lower load bearing surfaces, the first height being greater than the diameter of the bone anchor.

12. The device of claim 11, including a screw locking mechanism configured to inhibit back-out of the bone anchor from the second portion.

13. The device of claim 12, wherein the screw locking mechanism includes a protruding portion and a spring.

14. A composite interbody spacer comprising:
a first portion shaped and sized for placement in an intervertebral disc space between an upper vertebral body and a lower vertebral body to separate the upper and lower vertebral bodies at a distance that provides proper spinal column function, the first portion being formed of a first material, the first portion being configured as a load bearing portion and having a first bore formed therein, the first bore having a surface shape; and
a second portion being formed of a second material, the second portion having an outer surface shape closely matching the surface shape of the first bore, the second portion being at least partially disposed within the first bore in a manner that reinforces the first bore and in a manner to interface with a bone anchor extending through the first bore,
wherein the outer surface of the second portion forms a continuous perimeter adjacent to the surface of the first bore such that the second portion substantially resists elastic yielding, and
wherein the first portion includes an upper bearing surface shaped and sized to bear loads applied from the upper vertebral body and having a lower bearing surface shaped and sized to bear loads applied from the lower vertebral body, and an outwardly facing front surface between the upper and bottom bearing surfaces, the first bore being formed in the front surface and one of the upper and bottom bearing surfaces.

15. The spacer of claim 14, wherein the second portion comprises edges shaped to correspond to the front surface said one of the upper and bottom surfaces.

16. The spacer of claim 14, wherein the first portion is a polymer and the second portion is a metal.

17. The spacer of claim 14, wherein the first portion includes a hollow region.

18. The spacer of claim 14, wherein the second portion is a tubular sleeve including an inner shoulder configured to engage and limit passage of a portion of a bone screw.

19. The spacer of claim 14, wherein the second portion is embedded entirely within the first bore.

20. The spacer of claim 14, wherein the second portion includes a second bore and a third bore formed therein and being partially disposed within the first bore in a manner that a first bone anchor can extend through the first and second bores and a second bone anchor can extend through the first and third bores.

21. The spacer of claim 20, wherein the second and third bores extend at different angles through the second portion.

22. A composite interbody spacer comprising:
a first portion formed of a first material, the first portion being shaped and sized for placement in an intervertebral disc space between an upper vertebral body and a lower vertebral body to separate the upper and lower vertebral bodies at a distance that provides proper spinal column function, and being configured for placement between the upper and the lower vertebra as a load bearing portion, the first portion having an upper surface shaped and sized to bear loads applied from the upper vertebral body and having a lower surface shaped and sized to bear loads applied from the lower vertebral body, the first portion also having a first bore formed therein; and
a second portion formed of a second material and disposed at least partially within the first bore of the first portion, the second portion having a second bore formed therein for receiving an anchor, the second portion being configured so that the second bore is formed at an oblique angle relative to the upper and lower surfaces of the first portion, such that an axis through the second bore intersects at least one of the first and second surfaces,
wherein the second bore is at least partially disposed within the first bore in a manner that a bone anchor can extend through the first and second bores, the second bore having an outer surface,
wherein the outer surface of the second bore forms a continuous perimeter adjacent to the surface of the first bore such that the second portion substantially resists elastic yielding.

23. The spacer of claim 22, wherein the first material is a non-metal material and the second material is a metal material.

24. The spacer of claim 22, wherein the first bore has a cylindrical shape.

25. The spacer of claim 22, wherein the first portion has a U-shape having a first end and a second end, and wherein the second portion extends from the first end to the second end, the first bore being formed in one of the first and second ends.

26. The spacer of claim 22, wherein the second bore is unthreaded.

27. The spacer of claim 22, wherein the first portion includes a hollow region.

28. The spacer of claim 22, wherein the second portion is a tubular sleeve including an inner shoulder configured to engage and limit passage of a portion of a bone screw.

29. The spacer of claim 22, wherein the first portion includes an upper surface, a bottom surface, and a front surface connecting the upper and bottom surfaces, the first bore being formed in the front surface and one of the upper and bottom surface.

30. The spacer of claim 22, wherein the second portion is embedded entirely within the first bore.

31. The spacer of claim 22, wherein the second portion includes a third bore formed therein and being partially disposed within the first bore in a manner that a first bone anchor can extend through the first and second bores and a second bone anchor can extend through the first and third bores.

32. The spacer of claim 31, wherein the second and third bores extend at different angles through the second portion.

* * * * *